(12) United States Patent
Berthet et al.

(10) Patent No.: US 11,946,864 B2
(45) Date of Patent: Apr. 2, 2024

(54) NANO ENCODING TECHNOLOGY FOR THE TRACKING OF INFORMATION IN LIQUID SAMPLES

(71) Applicants: INSTITUT PASTEUR DE DAKAR, Dakar (SN); François Xavier Berthet, Barcelona (ES)

(72) Inventors: François Xavier Berthet, Barcelona (ES); Amadou Alpha Sall, Dakar (SN)

(*) Notice: Subject to any disclaimer, the term of this patent is extended or adjusted under 35 U.S.C. 154(b) by 363 days.

(21) Appl. No.: 17/052,136

(22) PCT Filed: Apr. 29, 2019

(86) PCT No.: PCT/EP2019/060965
§ 371 (c)(1),
(2) Date: Oct. 30, 2020

(87) PCT Pub. No.: WO2019/211246
PCT Pub. Date: Nov. 7, 2019

(65) Prior Publication Data
US 2021/0116375 A1 Apr. 22, 2021

(30) Foreign Application Priority Data
Apr. 30, 2018 (EP) .................................. 18170123

(51) Int. Cl.
| *B82Y 10/00* | (2011.01) |
| *B82Y 15/00* | (2011.01) |
| *B82Y 20/00* | (2011.01) |
| *B82Y 99/00* | (2011.01) |
| *C09K 11/56* | (2006.01) |
| *C09K 11/66* | (2006.01) |

(Continued)

(52) U.S. Cl.
CPC .......... *G01N 21/6428* (2013.01); *B82Y 10/00* (2013.01); *B82Y 15/00* (2013.01); *B82Y 20/00* (2013.01); *B82Y 99/00* (2013.01); *C09K 11/56* (2013.01); *C09K 11/661* (2013.01); *C09K 11/883* (2013.01); *G01N 33/58* (2013.01); *G06Q 10/0833* (2013.01); *B82Y 35/00* (2013.01); *G01N 2021/6439* (2013.01)

(58) Field of Classification Search
None
See application file for complete search history.

(56) References Cited

U.S. PATENT DOCUMENTS

| 6,544,732 | B1 * | 4/2003 | Chee | G01N 33/588 |
| | | | | 436/805 |
| 6,602,671 | B1 * | 8/2003 | Bawendi | G01N 33/588 |
| | | | | 435/7.1 |

(Continued)

OTHER PUBLICATIONS

Nie et al. ("Quantum-dot tagged microbreads," Nature Publishing Group, vol. 19, Jul. 2001, pp. 631-635) (Year: 2001).*

(Continued)

*Primary Examiner* — Neil N Turk
(74) *Attorney, Agent, or Firm* — SEED INTELLECTUAL PROPERTY LAW GROUP LLP (57) ABSTRACT

In the present invention, fluorescence properties of quantum dots are used to create or provide a chemical link between biological liquid samples and their associated digital information; thereby, facilitating an easy access and on-demand to all the information associated with the liquid biological sample.

20 Claims, 4 Drawing Sheets

| CATEGORY | | LOCATION | DATA TYPE | EXAMPLES |
|---|---|---|---|---|
| | ANALYTICAL DATA | INSIDE SAMPLE | Binary Alphanumeric Text + drawings Graphs | Biological sequences Chemical concentrations Clinical results MALDI/TOF Elementary analysis, etc. |
| | CONTEXTUAL DATA | OUTSIDE SAMPLE | Binary Images Video Sounds | GPS, maps, photos Videos, temperature, AR/VR, altitude, etc. |
| | HISTORICAL DATA | OUTSIDE SAMPLE | Binary Chronology Genealogy Multimedia | Texts, interviews, photos, drawings, books, 3D models, Database references, URL addresses, etc. |

(51) Int. Cl.
    *C09K 11/88*     (2006.01)
    *G01N 21/64*     (2006.01)
    *G01N 33/58*     (2006.01)
    *G06Q 10/0833*     (2023.01)
    *B82Y 35/00*     (2011.01)

(56) References Cited

U.S. PATENT DOCUMENTS

| | | | |
|---|---|---|---|
| 6,680,211 B2* | 1/2004 | Barbera-Guillem | ............................ G07D 7/1205 428/407 |
| 7,044,376 B2* | 5/2006 | Nelson | .................... G06K 1/121 235/454 |
| 2002/0077718 A1* | 6/2002 | Harburda | .............. G06Q 10/087 700/106 |
| 2009/0297448 A1* | 12/2009 | Yan | .................. G01N 33/54366 424/490 |
| 2010/0046825 A1* | 2/2010 | Haushalter | ............ B29C 45/372 382/141 |
| 2012/0187341 A1 | 7/2012 | Strek et al. | |
| 2014/0193841 A1* | 7/2014 | Welch | .................... B82Y 15/00 435/7.92 |

OTHER PUBLICATIONS

Liu et al., "Nanocrystal-Based Bioelectronic Coding of Single Nucleotide Polymorphisms," *Journal of the American Chemical Society* 127:38-39, 2005. [Published Online Dec. 2004] (8 pages).

Wang et al., "Electrochemical Coding Technology for Simultaneous Detection of Multiple DNA Targets," *Journal of the American Chemical Society* 125:3214-3215, Mar. 2003. (6 pages).

\* cited by examiner

Fig. 1

| CATEGORY | LOCATION | DATA TYPE | EXAMPLES |
|---|---|---|---|
| ANALYTICAL DATA | INSIDE SAMPLE | Binary Alphanumeric Text + drawings Graphs | Biological sequences Chemical concentrations Clinical results MALDI/TOF Elementary analysis, etc. |
| CONTEXTUAL DATA | OUTSIDE SAMPLE | Binary Images Video Sounds | GPS, maps, photos Videos, temperature, AR/VR, altitude, etc. |
| HISTORICAL DATA | OUTSIDE SAMPLE | Binary Chronology Genealogy Multimedia | Texts, interviews, photos, drawings, books, 3D models, Database references, URL addresses, etc. |

| DIGIT | first | second | third | fourth | fifth | sixth |
|---|---|---|---|---|---|---|
| Fluorophore | QDA | QDB | QDC | QDD | QDE | QDF |

| Name | Fluo QREF % | Fluo QDA % | Fluo QDB % | Fluo QDC % | Fluo QDD % | Fluo QDE % | Fluo QDF % | UNIQUE SIGNATURE |
|---|---|---|---|---|---|---|---|---|
| Sample 1 | 100 | 100 | 50 | 30 | 10 | 20 | 100 | 053120 |
| Sample 2 | 100 | 10 | 30 | 50 | 60 | 70 | 10 | 135671 |
| Sample 3 | 100 | 100 | 50 | 30 | 20 | 20 | 100 | 053220 |
| Sample 4 | 100 | 60 | 50 | 40 | 90 | 80 | 100 | 654980 |
| Sample 5 | 100 | 10 | 20 | 30 | 40 | 50 | 60 | 123456 |

NANO ENCODING TECHNOLOGY FOR THE TRACKING OF INFORMATION IN LIQUID SAMPLES

FIELD OF THE INVENTION

The present invention relates to quantum dots, and more particularly to the use of quantum dots for tagging liquid biological samples.

BACKGROUND OF THE INVENTION

Quantum dots, including their optical and physical properties and methods of manufacture, are well known and described in the following publications:
1. Warren C. W. Chan, Shuming Nie, "Quantum Dot Bioconjugates for Ultrasensitive Nonisotopic Detection", Science 281 (5385):2016
2. Marcel Burchez Jr., Mario Moronne, Peter Gin, Shimon Weiss, A. Paul Alivisatos, "Semiconductor nanocrystals as Fluorescent Biological Labels", 281 (5385):2013
3. L. E. Brus, Applied Physics A 53, 465 (1991)
4. W. L. Wilson, P. F. Szajowski, L. E. Brus, Science 262, 1242 (1993)
5. A. Henglein, Chem. Rev. 89, 1861 (1989)
6. H. Weller, Angew. Chem. Int. Ed. Engl. 32, 41 (1993)
7. M. A. Hines and P. Guyot-Sionnest, J. Phys. Chem. 100, 468 (1996)
8. B. O. Dabbousi, et al., J. Phys. Chem. B 101, 9463 (1997)
9. C. B. Murray, D. J. Norris, M. G. Bawendi, J. Am. Chem. Soc. 115, 8706 (1993)
10. X. G. Peng, J. Wickham, A. P. Alivasatos, J. Am. Chem. Soc. 120, 5343 (1998)
11. L. M. Lizmarzan, M. Giersig, P. Mulvaney, Langmuir 12, 4329 (1996)
12. M. A. CorreaDuarte, M. Giersig, L. M. LizMarzan, Chem. Phys. Lett. 286, 497 (1998)
13. Marcel Bruchez Jr., Mario Moronne, Peter Gin, Shimon Weiss, and A. Paul Alivisatos, "Semiconductor Nanocrystals as Fluorescent Biological Labels" Science 1998 Sep. 25; 281:2013-2016.
14. Warren C. W. Chan and Shuming Nie, "Quantum Dot Bioconjugates for Ultrasensitive Nonisotopic Detection" Science 1998 Sep. 25; 281:2016-2018.

The above publications describe methods for making quantum dots such as nanometer-sized crystals of CdSe—CdS and ZnS-capped CdSe. The publications also describe physical and optical properties of these quantum dots.

We herein and for the first time, use the fluorescence properties of quantum dots to create or provide a chemical link between biological liquid samples and their associated digital information.

BRIEF DESCRIPTION OF THE INVENTION

A first aspect of the present invention refers to the use of the fluorescence properties of quantum dots to create or provide a chemical link between biological liquid samples and their associated digital information.

A second aspect of the present invention refers to a chemical nanosignature composition useful or suitable for the tracking of information in liquid samples or for creating a chemical link between liquid biological samples and their associated digital information, which comprises a combination of at least one quantum dot reference and at least 2, 3, 4, 5 or more quantum dot tracers.

In a preferred embodiment of the second aspect of the invention, said quantum dots tracers, can be selected from a list comprising or consisting of any of the following or any combination thereof:
a. CdSeS/ZnS alloyed quantum dots;
b. CdSeS/ZnS alloyed quantum dots;
c. CdSe/ZnS core-shell type quantum dots;
d. CdSe/ZnS core-shell type quantum dots stabilized with octadecylamine ligands; and/or
e. CdTe core-type quantum dots COOH functionalized.

In another preferred embodiment of the second aspect of the invention, said quantum dot reference is PbS core-type quantum dots, preferably oleic acid coated.

In yet another preferred embodiment of the second aspect of the invention, the composition is in the form of a solution, preferably in the form of stock solutions.

A third aspect of the invention refers to a liquid biological sample comprising the composition useful or suitable for the tracking of information in liquid samples or for creating a chemical link between liquid biological samples and their associated digital information, identified or referred to in the second aspect of the invention.

A fourth aspect of the invention refers to the use of the composition of the second aspect of the invention, for creating a chemical link between liquid biological samples and their associated digital information.

A fifth aspect of the invention, refers to a method for creating a chemical link between liquid biological samples and their associated digital information, which comprises, sample tagging a liquid biological sample with a composition according to the second aspect of the invention, wherein said link is preferably created by using the following ratio:

$$\frac{\text{Tracer Fluo. Intensity}}{\text{Reference } Fluo \text{ Intensity}}$$

to normalized the fluorescence intensity of each tracer of the composition and arrayed said normalized values into a unique 2, 3, 4, 5, 6 or more digit number/signature, wherein said digit number/signature shall be read and be entered into a database at point of manufacture or point of application in order to create a chemical link between the liquid biological sample tagged with the composition of any of claims 2 to 5, and its associated digital information.

A sixth aspect of the invention refers to a method for tracking information in liquid biological samples, which comprises:
a. creating a chemical link between liquid biological samples and their associated digital information according to the fifth aspect of the invention; and
b. reading the fluorescence emission spectrum at the wavelength corresponding to each tracer to deciphered the digit number/signature to access the digital information of the liquid biological sample. Preferably, said fluorescence measurement is achieved by using a multi-wavelength fluorimeter (desktop or handheld) or a mobile device equipped with Lens-free fluorescence microscopy.

DETAILED DESCRIPTION OF THE INVENTION

In accordance with one aspect of the invention, fluorescence properties of quantum dots are used to create or provide a chemical link between biological liquid samples and their associated digital information; thereby, facilitating an easy access and on-demand to all the information associated with the liquid biological sample.

Figure 1:
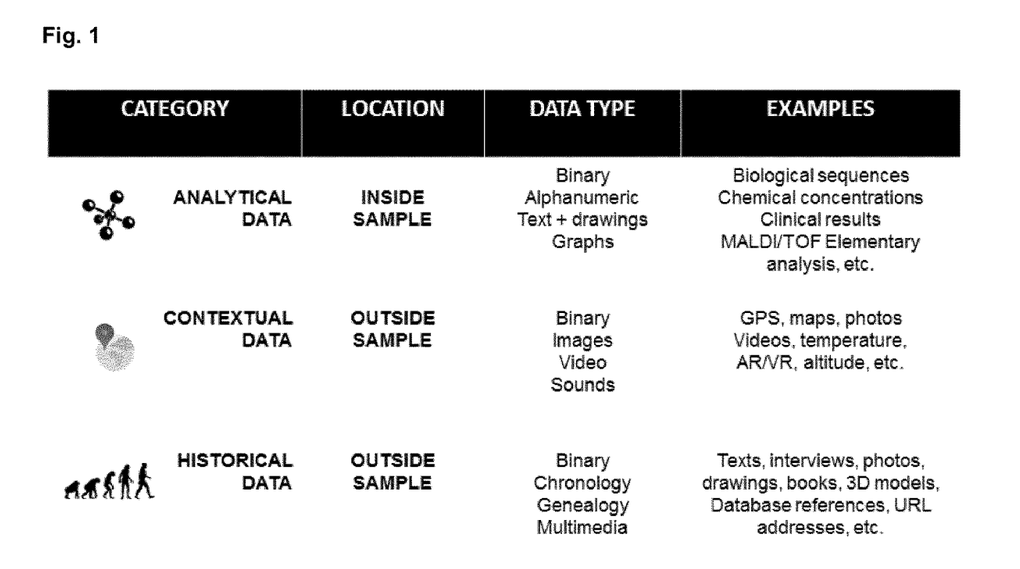
FIG. 1. This figure shows that information relating to a sample can be classified into at least three categories: ANALYTICAL CONTENT—Information relating to sample content, such as chemical & biochemical composition, pH, presence/absence of a given entity, etc. CONTEXTUAL CONTENT—Information and metadata relating to the sample environment, such as the place where the sample was collected, the name of the patient, etc. and HISTORICAL CONTENT—information relating to the reconstruction of past, present or future questions such as forensic examinations, paleontological investigations or evolutionary studies.

Samples from biological, organic, or inorganic compounds are the basic starting materials of many industries such as human and veterinary medicine, clinical diagnostics, food & beverage, bio banking, ecological conservation, climate reconstruction and mining. As represented in FIG. 1, the information relating to a sample can be classified into at least three categories:
ANALYTICAL CONTENT—Information relating to sample content, such as chemical & biochemical composition, pH, presence/absence of a given entity, etc.
CONTEXTUAL CONTENT—Information and metadata relating to the sample environment, such as the place where the sample was collected, the name of the patient, etc.
HISTORICAL CONTENT—information relating to the reconstruction of past, present or future questions such as forensic examinations, paleontological investigations or evolutionary studies.

The value of collecting samples relies upon the capacity to retrieve, easily, quickly and on-demand all the information associated with it, in order to take economically, socially or environmentally important decisions such as clinical diagnostics, food safety, climate change, outbreak management, etc.

Since the various sources of information associated with a given sample are generated by different players, in different locations (site of collect, site of processing, site of storage), and at different points in time, it is very difficult to access, analyze and display this information. This situation is particularly problematic for samples collected in remote locations and/or in low resource settings.

Figure 2:
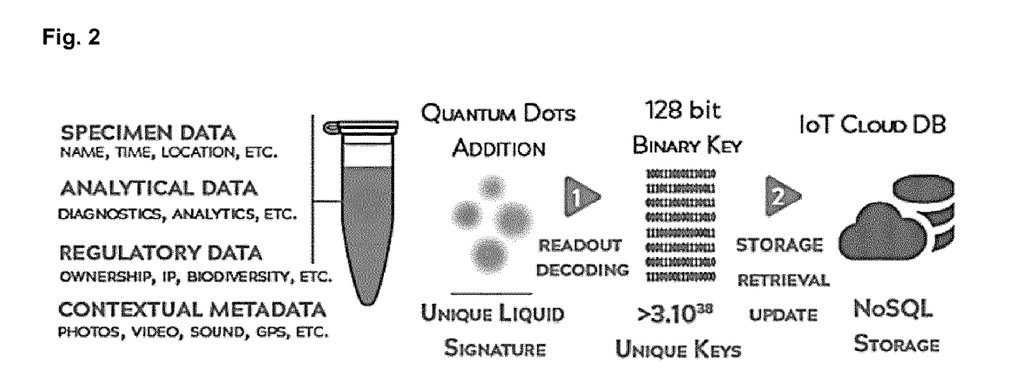
FIG. 2. This figure indicates the main steps connected to the Nano Encoding Technology of the present invention:
1. Sample tagging with a unique Quantum Dots (QD's) signature
2. Read-out of sample fluorescence
3. Deconvolution of QD's signature into a unique database address
4. Access, retrieve & update sample information FIG. 3. This figure shows a possible rule for determining the addition of tracers to a liquid biological sample and for creating a chemical link between the biological liquid samples and their associated digital information.

We herein describe a new workflow or methodology to create a chemical link between samples, preferably liquid biological samples, and their associated digital information. The workflow is named NETTALLIS, standing for "Nano Encoding Technology for the Tracking of information in Liquid Samples". As indicated in FIG. 2, it relies upon 4 major steps:
1. Sample tagging with a unique Quantum Dots (QD's) signature
2. Read-out of sample fluorescence
3. Deconvolution of QD's signature into a unique database address
4. Access, retrieve & update sample information NETTALLIS is advantageous since it allows life-long sample-tracking, multiple sample interrogation (pre-, post- and analytical stage of diagnostics), identification of sample cross contamination, and facilitates sample management, bio-banking and data sharing.

The use of quantum dots in accordance with various embodiments of the invention are illustrated in the examples explained below. It is, however, noted that a quantum-dot tagged liquid biological sample to provide a chemical link between said biological liquid sample and their associated digital information, may be made by using any type of quantum dots. In this sense, it is herein noted that quantum dots are very small semiconductor particles, only several nm in size, so small that their optical and electronic properties differ from those of larger particles. Many types of quantum dot will emit light of specific frequencies if electricity or light is applied to them, and these frequencies can be precisely tuned by changing the dots' size, shape and material, giving rise to many applications. Quantum dots exhibit properties that are intermediate between those of bulk semiconductors and those of discrete molecules. Their optoelectronic properties change as a function of both size and shape. Larger QDs (radius of 5-6 nm, for example) emit longer wavelengths resulting in emission colors such as orange or red. Smaller QDs (radius of 2-3 nm, for example) emit shorter wavelengths resulting in colors like blue and green, although the specific colors and sizes vary depending on the exact composition of the QD.

Therefore, a chemical nanosignature useful or suitable for the tracking of information in liquid samples or for creating a chemical link between samples, preferably liquid biological samples, and their associated digital information, can be any composition (from hereinafter chemical nanosignature composition), preferably in the form of a solution, that assembles a combination of at least one reference and at least 2, 3, 4, 5 or more quantum dot tracers. Said chemical nanosignature composition shall encode a 2, 3, 4, 5 or more-digits code depending on the number of tracers used. Said code should alone or in combination with further codes conform a chemical link between a biological liquid sample and its associated digital information.

For mere illustrative purposes, quantum dots useful as tracers to create the chemical nanosignature of the present invention, can be selected from any of the following or any combination thereof:
- CdSeS/ZnS alloyed quantum dots;
- CdSeS/ZnS alloyed quantum dots;
- CdSe/ZnS core-shell type quantum dots;
- CdSe/ZnS core-shell type quantum dots stabilized with octadecylamine ligands; and/or
- CdTe core-type quantum dots COOH functionalized.

In this sense, in a preferred embodiment, the invention refers to a chemical nanosignature composition, preferably in the form of a solution, useful or suitable for the tracking of information in liquid samples or for creating a chemical link between samples, preferably liquid biological samples, and their associated digital information, which comprises at least 2, 3, 4, or 5 or any combination thereof, of the quantum dots selected from the following list:
- CdSeS/ZnS alloyed quantum dots;
- CdSeS/ZnS alloyed quantum dots;
- CdSe/ZnS core-shell type quantum dots;
- CdSe/ZnS core-shell type quantum dots stabilized with octadecylamine ligands; and/or
- CdTe core-type quantum dots COOH functionalized.

It is herein noted, that the chemical chemical nanosignature composition of the present invention shall further comprise a control reference. Such control reference, may be PbS core-type quantum dots oleic acid coated.

Figure 4:
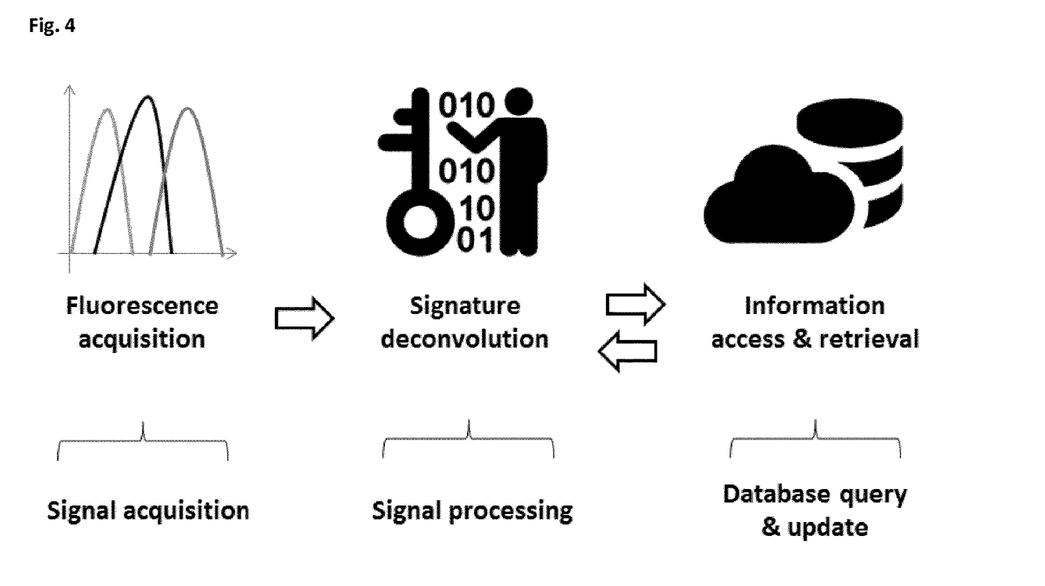
FIG. 4. This figure shows, the single acquisition and the deconvolution process achieved by reading the fluorescence emission spectrum at the wavelength corresponding to each tracer and by attributing a finite rational value for each emission maxima.

Preferably, and as illustrated in the examples of the present invention, as reflected in the following ratio:

$$\frac{\text{Tracer Fluo. Intensity}}{\text{Reference } Fluo \text{ Intensity}}$$

the fluorescent signal emitted by each tracer of the chemical nanosignature composition, will be normalized (using QREF as a reference) and arrayed into a unique 2, 3, 4, 5, 6 or more digit number/signature. This number shall be used as a query to access a unique database address thus creating a chemical link between samples, preferably liquid biological samples, and their associated digital information The overall process is presented in FIG. 4.

In another preferred embodiment of the invention, the chemical nanosignature composition, preferably in the form of a solution, useful or suitable for the tracking of information in liquid samples or for creating a chemical link between samples, preferably liquid biological samples, and their associated digital information, is in the form of stock solutions comprising unique cocktails containing a combination of 1 reference+2, 3, 4, or 5 or more tracers, preferably 5 tracers, in order to encode a 2, 3, 4, 5 or more-digits code.

It is herein further noted that said chemical nanosignature composition may further comprise any type of quantum dots, as long as these (each type of quantum dot) act as a tracer emitting a fluorescent signal or emission spectrum at a particular wavelength, wherein said fluorescent signal or intensity shall be normalized for each of tracers conforming the chemical nanosignature and arrayed in the above said unit digit number/signature. In this sense, and just as a mere example of the invention, quantum dots can made of any of CdSe quantum dots surrounded by a cap of ZnSe. The ZnSe-capped CdSe quantum dots are prepared by known methods, and have a distinctive distribution of sizes and optical properties of light emitted by the dots. For example, centrifugation can be employed to separate quantum dots according to size due to their size-dependent precipitation rates.

In addition, and as described in the examples, once the liquid biological sample has been tagged with the chemical nanosignature of the invention with a unique Quantum Dots (QD's) signature, deconvolution is achieved by reading the fluorescence emission spectrum at the wavelength corresponding to each tracer and by attributing a finite rational value for each emission maxima. This fluorescence measurement can be achieved using a multi-wavelength fluorimeter (desktop or handheld) or a mobile device equipped with Lens-free fluorescence microscopy.

Because the fluorescence pattern on each tracer is unique and a mixture of quantum dots thus conforms a unique signature, fluorescence patterns for each chemical nanosignature of the present invention shall be read and be entered into a database at point of manufacture or point of application. Then at point of sale or at distribution points, the fluorescence patterns may be read and matched to patterns in the database, thereby creating or providing the chemical link between biological liquid samples and their associated digital information.

It is to be understood that even though various embodiments and advantages of the present invention have been set forth in the foregoing description, the above disclosure is illustrative only, and changes may be made in detail, and yet remain within the broad principles of the invention. Therefore, the present invention is to be limited only by the appended claims.

EXAMPLES

Example 1—Creation of Unique Quantum Dots (QD) Signatures

Quantum dots are very small semiconductor particles, only several nm in size, so small that their optical and electronic properties differ from those of larger particles. Many types of quantum dot will emit light of specific frequencies if electricity or light is applied to them, and these frequencies can be precisely tuned by changing the dots' size, shape and material, giving rise to many applications. Quantum dots exhibit properties that are intermediate between those of bulk semiconductors and those of discrete molecules. Their optoelectronic properties change as a function of both size and shape. Larger QDs (radius of 5-6 nm, for example) emit longer wavelengths resulting in emission colors such as orange or red. Smaller QDs (radius of 2-3 nm, for example) emit shorter wavelengths resulting in colors like blue and green, although the specific colors and sizes vary depending on the exact composition of the QD.

For the purpose of creating unique signatures, we used various kinds of quantum dots purchased at Sigma Aldrich:

TABLE 1

| Product Reference | Description | Code name | Maximal Fluorescence Emission | Final Concentration Of use |
|---|---|---|---|---|
| 753793 | CdSeS/ZnS alloyed quantum dots | QDA | 630 nm | 0.2-5 microM |
| 753742 | CdSeS/ZnS alloyed quantum dots | QDB | 450 nm | 0.2-5 microM |
| 748742 | CdSe/ZnS core-shell type quantum dots | QDC | 540 nm | 0.2-5 microM |

TABLE 1-continued

| Product Reference | Description | Code name | Maximal Fluorescence Emission | Final Concentration Of use |
|---|---|---|---|---|
| 790192 | CdSe/ZnS core-shell type quantum dots stabilized with octadecylamine ligands | ODE | 620 nm | 0.2-5 microM |
| 777951 | CdTe core-type quantum dots COOH functionalized | QDF | 610 nm | 0.2-5 microM |
| 747017 | PbS core-type quantum dots oleic acid coated | QREF | 1000 nm | 2 microM |

Figure 3:
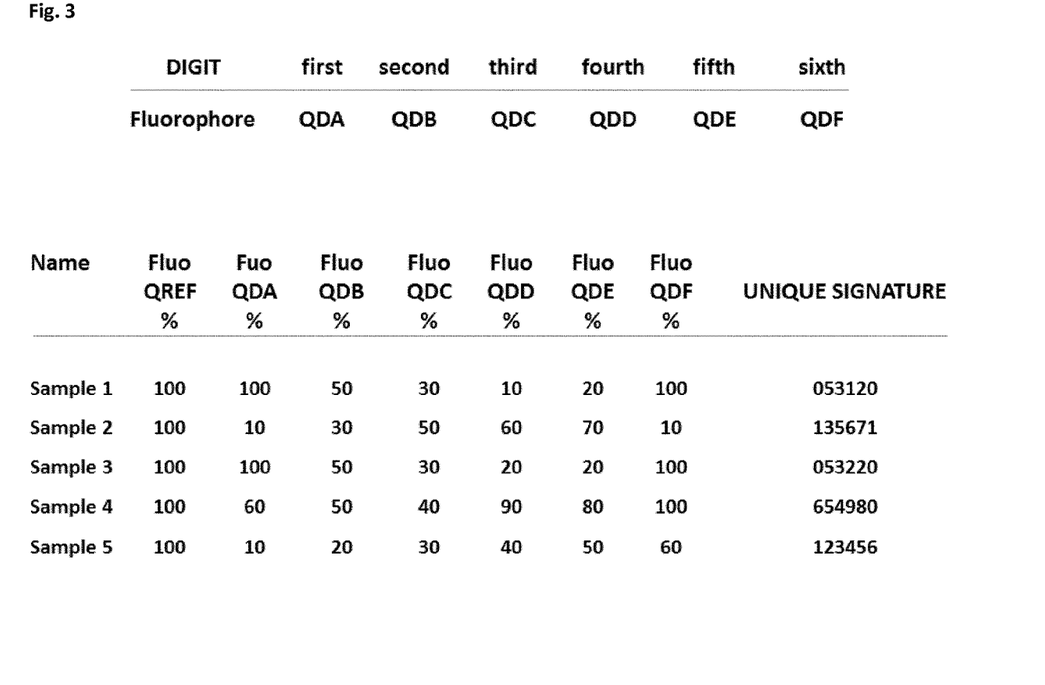

Stock solutions (500×, 1 mM) of reference (QREF) & tracers (QDA, QDB, QDC, QDE & QDF) were prepared in Toluene, and stored frozen at −20 C. Stock solutions were used to assemble unique cocktails containing a combination of 1 reference+5 tracers in order to encode a 5-digit code. As shown in FIG. 3, the rule determining the addition of tracers was the following:

TABLE 2

| Ratio = $\dfrac{\text{Tracer Fluo. Intensity}}{\text{Reference } Fluo \text{ Intensity}}$ | Encoded Signature QD Digit |
|---|---|
| 10/10 | 0 |
| 9/10 | 9 |
| 8/10 | 8 |
| 7/10 | 7 |
| 6/10 | 6 |
| 5/10 | 5 |
| 4/10 | 4 |
| 3/10 | 3 |
| 2/10 | 2 |
| 1/10 | 1 |

Example 2—Deconvolution of QD Signatures into a Database Address and Information Access Deconvolution is achieved by reading the fluorescence emission spectrum at the wavelength corresponding to each tracer and by attributing a finite rational value for each emission maxima. This fluorescence measurement can be achieved using a multi-wavelength fluorimeter (desktop or handheld) or a mobile device equipped with Lens-free fluorescence microscopy.

Once acquired, the fluorescent signal will be normalized (using QREF as a reference) and arrayed into a unique 6 digit number/signature. This number is used as a query to access a unique database address. The overall process is presented in FIG. 4.

Example 4—Convolution and Deconvolution of Fluorescent Quantum Dots Tags

The following quantum dots probes were used:

| Probe | λ excitation used | λ emission detected | Supplier |
|---|---|---|---|
| Qdot 525 | 350 nm or 488 nm | 525 nm | ThermoFischer (Invitrogen) |
| Qdot 565 | 350 nm or 488 nm | 565 nm | ThermoFischer (Invitrogen) |
| Qdot 605 | 350 nm or 488 nm | 605 nm | ThermoFischer (Invitrogen) |
| Qdot 655 | 350 nm or 488 nm | 655 nm | ThermoFischer (Invitrogen) |
| Qdot 705 | 350 nm or 633 nm | 705 nm | ThermoFischer (Invitrogen) |

Convolution: pure quantum dots or conjugated derivatives (such as Streptavidin, antibody or wheat conjugates) were used to prepare stock solutions containing fluorophores at a concentration ranging from 5 to 50 nM, phosphate, Tris or Hepes buffer. The 100% of fluorescence was measured with a solution of Qdot 705. In addition to the Qdot705 reference fluorophore, signatures were assembled by adding different amount of Qdot525, Qdot565, Qdot605, & Qdot655 into the same test solution. To correct variations due to differences in solution/buffer quenching, quantum yield, etc., the amount of each quantum dot was adjusted so that the corresponding emitted fluorescence would be of the form: n/10 with n being an integer from the list 1, 2, 3, 4, 5, 6, 7, 8, 9, or 10.

Deconvolution: samples were excited with a wavelength of 350 nm and the intensity of fluorescence emission was recorded at 525 nm, 565 nm, 605 nm, 655 nm, & 705 nm. Signals were expressed as a percentage of the reference (Qdot 705 taken as 100%) and values were rounded to closest multiple of ten using the floor or ceiling functions provided by the Mathematica software package (Wolfram).

Example of deconvoluted signatures: the following table represents some of the signatures generated to demonstrate the possibilities of the NETTALIS technology. A table summarizing the deconvoluted tags is presented below:

| Relative fluorescence | Test tag 1 | Test tag 2 | Test tag 3 | Test tag 4 |
|---|---|---|---|---|
| Qdot705 (%) | 100 | 100 | 100 | 100 |
| QDot525 (%) | 10 | 40 | 30 | 20 |
| QDot565 (%) | 90 | 10 | 10 | 70 |
| QDot605 (%) | 60 | 40 | 40 | 10 |
| QDot665 (%) | 90 | 30 | 10 | 80 |
| Deconvoluted signal | 1969 | 4143 | 3141 | 2718 |

Figure 5:
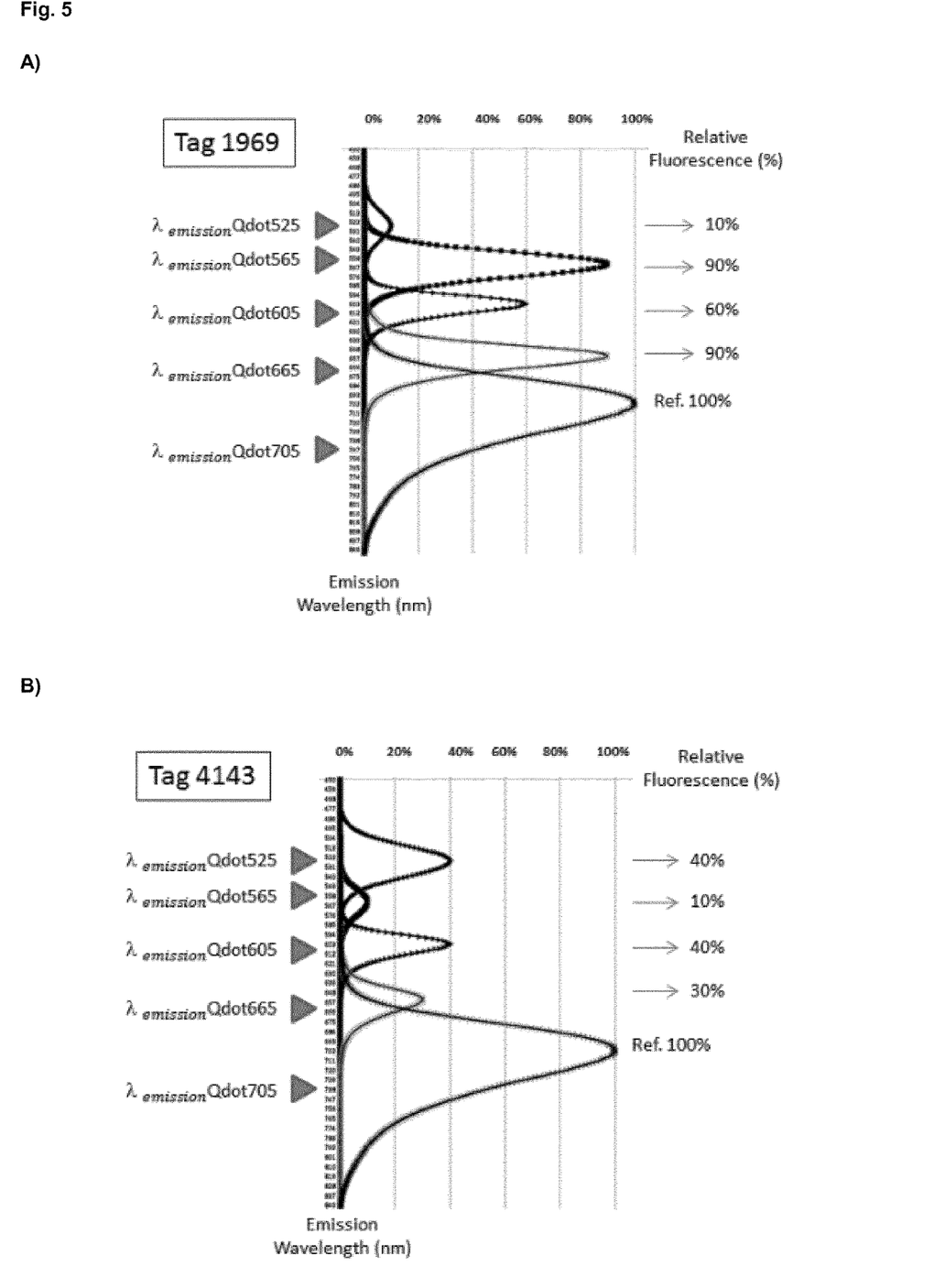
FIG. 5. This figure shows the emission spectrum and deconvolution of quantum dots signature tags. For each tag, relative fluorescence emission was measured at 525 nm, 565 nm, 605 nm, 665 nm & 705 nm. Relative fluorescence intensity was normalized considering the intensity of Qdot705 as 100%. The following quantum dots signatures were analyzed: (5A) nanosignature tag encoding the numerical sequence {1,9,6,9}, (5B) nanosignature tag encoding the numerical sequence {4,1,4,3}, (5C) nanosignature tag encoding the numerical sequence {3,1,4,1}, (5D) nanosignature tag encoding the numerical sequence {2,7,1,8}.

A graphical representation was generated using the online tool Spectra Viewer (Thermofisher) and is presented in FIG. 5.

The invention claimed is:

1. A method for creating a chemical link between liquid biological samples and their associated digital information, which comprises, tagging a liquid biological sample with a chemical nanosignature composition which comprises a combination of at least one quantum dot reference and at least 2, 3, 4, 5 or more quantum dot tracers, wherein said link is created by using the following ratio:

$$\dfrac{\text{Tracer Fluo. Intensity}}{\text{Reference } Fluo \text{ Intensity}}$$

to obtain a single encoded digit for each individual quantum dot tracer, wherein Tracer Fluo. Intensity is the fluorescence intensity of the individual quantum dot tracer, and Reference Fluo. Intensity is the fluorescence intensity of the quantum dot reference, and arraying said single encoded digits into a unique 2, 3, 4, 5, 6 or more digit numerical signature, wherein said numerical signature is read and entered into a database at a point of manufacture or a point of application in order to create a chemical link between the liquid biological sample tagged with the chemical nanosignature composition, and its associated digital information.

2. A method for tracking information in liquid biological samples, which comprises:
   a. creating a chemical link between liquid biological samples and their associated digital information according to claim 1; and
   b. reading a fluorescence emission spectrum at a wavelength corresponding to each tracer to decipher the unique digit signature to access the digital information of the liquid biological sample.

3. The method of claim 2, wherein fluorescence measurement is achieved by using a desktop or handheld multiwavelength fluorimeter or a mobile device equipped with Lens-free fluorescence microscopy.

4. The method of claim 1, wherein said quantum dot tracers are selected from any of the following and any combination thereof:
   a. CdSeS/ZnS alloyed quantum dots;
   b. CdSeS/ZnS alloyed quantum dots;
   c. CdSe/ZnS core-shell type quantum dots;
   d. CdSe/ZnS core-shell type quantum dots stabilized with octadecylamine ligands; and
   e. CdTe core-type quantum dots COOH functionalized.

5. The method of claim 1, wherein said quantum dot reference is PbS core-type quantum dots.

6. The method of claim 1, wherein said chemical nanosignature composition is in the form of a solution.

7. The method of claim 5, wherein said quantum dot reference is oleic acid coated.

8. The method of claim 6, wherein said solution is in the form of a stock solution.

9. The method of claim 2, wherein said quantum dot tracers are selected from any of the following and any combination thereof:
   a. CdSeS/ZnS alloyed quantum dots;
   b. CdSeS/ZnS alloyed quantum dots;
   c. CdSe/ZnS core-shell type quantum dots;
   d. CdSe/ZnS core-shell type quantum dots stabilized with octadecylamine ligands; and
   e. CdTe core-type quantum dots COOH functionalized.

10. The method of claim 3, wherein said quantum dot tracers are selected from any of the following and any combination thereof:
   a. CdSeS/ZnS alloyed quantum dots;
   b. CdSeS/ZnS alloyed quantum dots;
   c. CdSe/ZnS core-shell type quantum dots;
   d. CdSe/ZnS core-shell type quantum dots stabilized with octadecylamine ligands; and
   e. CdTe core-type quantum dots COOH functionalized.

11. The method of claim 2, wherein said quantum dot reference is PbS core-type quantum dots.

12. The method of claim 11, wherein said quantum dot reference is oleic acid coated.

13. The method of claim 3, wherein said quantum dot reference is PbS core-type quantum dots.

14. The method of claim 13, wherein said quantum dot reference is oleic acid coated.

15. The method of claim 4, wherein said quantum dot reference is PbS core-type quantum dots.

16. The method of claim 15, wherein said quantum dot reference is oleic acid coated.

17. The method of claim 2, wherein said chemical nanosignature composition is in the form of a solution.

18. The method of claim 3, wherein said chemical nanosignature composition is in the form of a solution.

19. The method of claim 4, wherein said chemical nanosignature composition is in the form of a solution.

20. The method of claim 5, wherein said chemical nanosignature composition is in the form of a solution.

* * * * *